(12) United States Patent
Thomas et al.

(10) Patent No.: US 7,731,988 B2
(45) Date of Patent: Jun. 8, 2010

(54) MULTI-POLYMER HYDROGELS

(75) Inventors: Brian Thomas, Columbia City, IN (US); Kai Zhang, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 372 days.

(21) Appl. No.: 11/833,549

(22) Filed: Aug. 3, 2007

(65) Prior Publication Data
US 2009/0035344 A1 Feb. 5, 2009

(51) Int. Cl.
 A61F 2/02 (2006.01)
 A61F 2/28 (2006.01)
 A61F 2/30 (2006.01)
(52) U.S. Cl. ..................... 424/423; 523/113
(58) Field of Classification Search ............... None
See application file for complete search history.

(56) References Cited

U.S. PATENT DOCUMENTS

| | | | |
|---|---|---|---|
| 3,862,265 A | 1/1975 | Steinkamp |
| 3,875,302 A | 4/1975 | Inoue |
| 4,036,788 A | 7/1977 | Steckler |
| 4,058,491 A | 11/1977 | Steckler |
| 4,060,678 A | 11/1977 | Steckler |
| 4,071,508 A | 1/1978 | Steckler |
| 4,279,795 A | 7/1981 | Yamashita |
| 4,300,820 A | 11/1981 | Shah |
| 4,379,874 A | 4/1983 | Stoy |
| 4,451,599 A | 5/1984 | Odorzynski |
| 4,451,630 A | 5/1984 | Atkinson |
| 4,464,438 A | 8/1984 | Lu |
| 4,472,542 A | 9/1984 | Nambu |
| 4,640,941 A | 2/1987 | Park |
| 4,663,358 A | 5/1987 | Hyon |
| 4,664,857 A | 5/1987 | Nambu |
| 4,734,097 A | 3/1988 | Tanabe |
| 4,771,089 A | 9/1988 | Ofstead |
| 4,772,287 A | 9/1988 | Ray |
| 4,808,353 A | 2/1989 | Nambu |
| 4,842,597 A | 6/1989 | Brook |
| 4,851,168 A | 7/1989 | Graiver |
| 4,859,719 A | 8/1989 | Ofstead |
| 4,871,490 A | 10/1989 | Rosiak |
| 4,874,562 A | 10/1989 | Hyon |
| 4,915,974 A | 4/1990 | D'Amelia |
| 4,966,924 A | 10/1990 | Hyon et al. |
| 4,988,761 A | 1/1991 | Ikada |
| 5,028,648 A | 7/1991 | Famili |
| 5,047,055 A | 9/1991 | Bao et al. |
| 5,053,455 A | 10/1991 | Kroggel |
| 5,118,779 A | 6/1992 | Szycher |
| 5,122,565 A | 6/1992 | George |
| 5,157,093 A | 10/1992 | Harisiades |
| 5,189,097 A | 2/1993 | LaFleur |
| 5,192,326 A | 3/1993 | Bao |
| 5,244,799 A | 9/1993 | Anderson |
| 5,288,503 A | 2/1994 | Wood |
| 5,306,311 A | 4/1994 | Stone |
| 5,311,223 A | 5/1994 | Vanderlaan |
| 5,315,478 A | 5/1994 | Cadwell |
| 5,334,634 A | 8/1994 | Bastiolo |
| 5,358,525 A | 10/1994 | Fox |
| 5,360,830 A | 11/1994 | Bastioli et al. |
| 5,362,803 A | 11/1994 | LaFleur |
| 5,410,016 A | 4/1995 | Hubbell |
| 5,458,643 A | 10/1995 | Oka |
| 5,527,271 A | 6/1996 | Shah |
| 5,552,096 A | 9/1996 | Auda |

(Continued)

FOREIGN PATENT DOCUMENTS

| | | |
|---|---|---|
| EP | 0290616 | 11/1988 |
| EP | 0365108 | 4/1990 |
| EP | 0505634 | 9/1992 |
| EP | 0696210 | 2/1996 |
| EP | 0784987 | 7/1997 |
| EP | 0845480 | 6/1998 |

(Continued)

OTHER PUBLICATIONS

Noguchi et al., Poly(vinyl Alcohol) Hydrogel As an Artificial Articular Cartilage: Evaluation of Biocompatibility, Journal of Applied Biomaterials, vol. 2, 101-107 (1991).
Jenkins et al., Glossary of Basic Terms in Polymer Science, Pure & Appl. Chem. vol. 68, No. 12, pp. 2287-2311 (1996).
Peppas et al., Structure and Applications of Poly(vinyl Alcohol) Hydrogels Produced by Conventional Crosslinking or by Freezaing/Thawing Methods, Adv. Polymer Sci. vol. 153, 37 (2000).
Bryant, S.J. et al. "Crosslinking Density Influences Chrondrocyte Metabolism in Dynamically Leaded Photocrosslinked Poly(ethylene glycol) Hydrogels." Ann. Biomed. Eng., Mar. 2004, pp. 407-417, vol. 3, No. 3.

(Continued)

*Primary Examiner*—Robert A Wax
*Assistant Examiner*—Danah Al-Awadi
(74) *Attorney, Agent, or Firm*—Woods Rogers PLC

(57) ABSTRACT

The invention provides a multi-polymer hydrogel article having a first polymeric, water-swellable material and a second polymeric material, organized such that a first region substantially comprises the first polymeric, water-swellable material, a second region adjacent the first region comprises a mixture of the first polymeric, water-swellable material and the second polymeric material, and a third region adjacent the second region substantially comprises the second polymeric material. The article exhibits an increasing concentration gradient of the second polymeric material moving from the first region, through the second region, to the third region. The invention also provides methods for forming a multi-polymer hydrogel article by (a) forming a hydrogel structure using a first polymeric, water-swellable material, (b) creating an aerogel structure having a plurality of open pores by dehydrating the hydrogel structure, (c) contacting the aerogel structure with a second polymeric material to incorporate the second polymeric material into at least a portion of the plurality of open pores to form the multi-polymer hydrogel article, and (d) rehydrating the multi-polymer hydrogel article.

28 Claims, No Drawings

U.S. PATENT DOCUMENTS

| | | |
|---|---|---|
| 5,580,938 A | 12/1996 | Gutweiler |
| 5,624,463 A | 4/1997 | Stone |
| 5,632,774 A | 5/1997 | Babian |
| 5,674,295 A | 10/1997 | Ray |
| 5,681,300 A | 10/1997 | Ahr |
| 5,709,854 A | 1/1998 | Griffith-Cima |
| 5,711,960 A | 1/1998 | Shikinami |
| 5,716,404 A | 2/1998 | Vacanti |
| 5,723,331 A | 3/1998 | Tubo et al. |
| 5,834,029 A | 11/1998 | Bellamkonda |
| 5,941,909 A | 8/1999 | Purkait |
| 5,976,186 A | 11/1999 | Bao |
| 5,981,826 A | 11/1999 | Ku |
| 6,015,576 A | 1/2000 | See |
| 6,017,577 A | 1/2000 | Hostettler |
| 6,040,493 A | 3/2000 | Cooke |
| 6,080,488 A | 6/2000 | Hostettler |
| 6,117,449 A | 9/2000 | See |
| 6,120,904 A | 9/2000 | Hostettler |
| 6,121,341 A | 9/2000 | Sawhney |
| 6,129,791 A | 10/2000 | Hubbell |
| 6,132,468 A | 10/2000 | Mansmann |
| 6,139,963 A | 10/2000 | Fujii |
| 6,156,345 A | 12/2000 | Chudzik |
| 6,156,572 A | 12/2000 | Bellamkonda |
| 6,162,456 A | 12/2000 | Dunbar |
| 6,180,132 B1 | 1/2001 | Huang |
| 6,180,606 B1 | 1/2001 | Chen et al. |
| 6,187,048 B1 | 2/2001 | Mitner |
| 6,207,185 B1 | 3/2001 | See |
| 6,211,296 B1 | 4/2001 | Frate |
| 6,224,893 B1 | 5/2001 | Langer |
| 6,231,605 B1 | 5/2001 | Ku |
| 6,232,406 B1 | 5/2001 | Stoy |
| 6,238,691 B1 | 5/2001 | Huang |
| 6,268,405 B1 | 7/2001 | Yao |
| 6,271,278 B1 | 8/2001 | Park et al. |
| 6,280,475 B1 | 8/2001 | Bao |
| 6,306,424 B1 | 10/2001 | Vyakarnam |
| 6,365,149 B2 | 4/2002 | Vyakarnam |
| 6,371,984 B1 | 4/2002 | Van Dyke |
| 6,372,283 B1 | 4/2002 | Shim |
| 6,375,634 B1 | 4/2002 | Carroll |
| 6,387,325 B1 | 5/2002 | Keusch |
| 6,402,784 B1 | 6/2002 | Wardlaw |
| 6,443,988 B2 | 9/2002 | Felt |
| 6,509,098 B1 | 1/2003 | Merrill |
| 6,531,147 B2 | 3/2003 | Sawhney |
| 6,533,817 B1 | 3/2003 | Norton |
| 6,608,117 B1 | 8/2003 | Gvozdic |
| 6,620,196 B1 | 9/2003 | Trieu |
| 6,626,945 B2 | 9/2003 | Simon |
| 6,629,997 B2 | 10/2003 | Mansmann |
| 6,630,457 B1 | 10/2003 | Aeschlimann |
| 6,632,246 B1 | 10/2003 | Simon |
| 6,645,517 B2 | 11/2003 | West |
| 6,692,738 B2 | 2/2004 | MacLaughlin |
| 6,706,690 B2 | 3/2004 | Reich |
| 6,709,668 B2 | 3/2004 | Won |
| 6,710,104 B2 | 3/2004 | Haraguchi |
| 6,710,126 B1 | 3/2004 | Hirt |
| 6,723,781 B1 | 4/2004 | Frate |
| 6,730,298 B2 | 5/2004 | Griffith-Cima |
| 6,733,533 B1 | 5/2004 | Lozier |
| 6,780,840 B1 | 8/2004 | DeVore |
| 6,783,546 B2 | 8/2004 | Zucherman |
| 6,783,721 B2 | 8/2004 | Higham |
| 6,803,420 B2 | 10/2004 | Cleary |
| 6,852,772 B2 | 2/2005 | Muratoglu |
| 6,855,743 B1 | 2/2005 | Gvozdic |
| 6,861,067 B2 | 3/2005 | McGhee |
| 7,235,592 B2 | 6/2007 | Muratoglu |
| 2001/0026810 A1 | 10/2001 | McGhee |
| 2001/0032019 A1 | 10/2001 | Van Dyke |
| 2001/0049417 A1 | 12/2001 | Frate |
| 2001/0053897 A1 | 12/2001 | Frate et al. |
| 2002/0022884 A1 | 2/2002 | Mansmann |
| 2002/0026244 A1 | 2/2002 | Trieu |
| 2002/0029083 A1 | 3/2002 | Zucherman |
| 2002/0049498 A1 | 4/2002 | Yuksel |
| 2002/0151979 A1 | 10/2002 | Lambrecht |
| 2002/0173855 A1 | 11/2002 | Mansmann |
| 2002/0193531 A1 | 12/2002 | Stoy |
| 2003/0008396 A1 | 1/2003 | Ku |
| 2003/0065389 A1 | 4/2003 | Petersen |
| 2003/0080465 A1 | 5/2003 | Higham |
| 2003/0130427 A1 | 7/2003 | Cleary |
| 2003/0170308 A1 | 9/2003 | Cleary |
| 2003/0195628 A1 | 10/2003 | Bao |
| 2003/0232895 A1 | 12/2003 | Omidian |
| 2003/0236323 A1 | 12/2003 | Ratner |
| 2004/0002764 A1 | 1/2004 | Gainor |
| 2004/0030392 A1 | 2/2004 | Lambrecht |
| 2004/0039447 A1 | 2/2004 | Simon |
| 2004/0092653 A1 | 5/2004 | Ruberti |
| 2004/0096509 A1 | 5/2004 | Hutchens |
| 2004/0116641 A1 | 6/2004 | Mather |
| 2004/0127618 A1 | 7/2004 | Ulmer |
| 2004/0127992 A1 | 7/2004 | Sehman |
| 2004/0131852 A1 | 7/2004 | Grinstaff |
| 2004/0133280 A1 | 7/2004 | Trieu |
| 2004/0143329 A1 | 7/2004 | Ku |
| 2004/0147673 A1 | 7/2004 | Calabro |
| 2004/0153163 A1 | 8/2004 | Posner |
| 2004/0161444 A1 | 8/2004 | Song |
| 2004/0171740 A1 | 9/2004 | Ruberti |
| 2004/0220296 A1 | 11/2004 | Lowman |
| 2004/0242770 A1 | 12/2004 | Feldstein |
| 2005/0027069 A1 | 2/2005 | Rhee et al. |
| 2005/0048103 A1 | 3/2005 | Cleary |
| 2005/0049365 A1 | 3/2005 | Cleary |
| 2005/0095296 A1 | 5/2005 | Lowman |
| 2005/0197441 A1 | 9/2005 | Shibutani |
| 2006/0188487 A1 | 8/2006 | Thomas |
| 2007/0004861 A1 | 1/2007 | Cai |
| 2007/0293651 A1 | 12/2007 | Tada |
| 2008/0090145 A1 | 4/2008 | Hiwara |

FOREIGN PATENT DOCUMENTS

| | | |
|---|---|---|
| EP | 0927053 | 7/1999 |
| EP | 1079224 | 2/2001 |
| EP | 1174463 | 1/2002 |
| EP | 1593400 | 11/2005 |
| EP | 1595899 | 11/2005 |
| FR | 2786400 | 6/2000 |
| FR | 2865939 | 8/2005 |
| JP | 01305959 | 12/1989 |
| JP | 03141957 | 6/1991 |
| JP | 04303444 | 10/1992 |
| JP | 09124730 | 5/1997 |
| JP | 09124731 | 5/1997 |
| JP | 10036524 | 2/1998 |
| JP | 10036534 | 2/1998 |
| JP | 10043286 | 2/1998 |
| JP | 10306534 | 2/1998 |
| WO | 9015082 | 12/1990 |
| WO | 9417851 | 8/1994 |
| WO | 9526699 | 10/1995 |
| WO | 9640304 | 4/1998 |
| WO | 9817215 | 4/1998 |
| WO | 9853768 | 12/1998 |
| WO | 9903454 | 1/1999 |
| WO | 9913923 | 3/1999 |

| | | |
|---|---|---|
| WO | 9967320 | 12/1999 |
| WO | 0117574 | 3/2001 |
| WO | 0177197 | 10/2001 |
| WO | 0213871 | 2/2002 |
| WO | 02060501 | 8/2002 |
| WO | 02087642 | 11/2002 |
| WO | 02087645 | 11/2002 |
| WO | 03008007 | 1/2003 |
| WO | 03074099 | 9/2003 |
| WO | 2004007651 | 1/2004 |
| WO | 2004029174 | 4/2004 |
| WO | 2004031253 | 4/2004 |
| WO | 2004047690 | 6/2004 |
| WO | 2004055057 | 7/2004 |
| WO | 2004060427 | 7/2004 |
| WO | 2004063388 | 7/2004 |
| WO | 2004064693 | 8/2004 |
| WO | 2004066704 | 8/2004 |
| WO | 2004069296 | 8/2004 |
| WO | 2004069296 A1 | 8/2004 |
| WO | 2004072138 | 8/2004 |
| WO | 2004093786 | 11/2004 |
| WO | 2005004943 | 1/2005 |
| WO | 2005035726 | 4/2005 |
| WO | 2006021054 | 3/2006 |
| WO | 2006091706 | 8/2006 |
| WO | 2007015208 | 8/2007 |

OTHER PUBLICATIONS

Bryant, S.J. et al. "The Effects if Scaffold thickness on Tissue Engineered Cartilage in Photocrosslinked Poly (ethylene oxide) hydrogels." Biomaterials 22, 2001, pp. 619-628.

Bryant, S.J. et al. "Photocrosslinkable Poly(ethylene oxide) and Poly (vinyl alcohol) Hydrogels for Tissue Engineering Cartilage." 21st Annual Conference and the 1999 Annual Fall Meeting of the Biomedical Engineering Society, Oct. 13-15, 1999, Atlanta, GA; Engineering in Medicine and Biology 1999, p. 751, vol. 2.

Durmaz, S. et al. "Phase Separation during the Formation of Poly(acrylamide) Hydrogels" Polymer 41, 2000, pp. 5729-5735.

Gong, J.P. et al. "Friction of Polymer Gels and the Potential Application as Artificial Cartilage." SPIE, Mar. 1999, pp. 218-225, vol. 3669.

Guilherme, R. et al. "Hydrogels based on PAAm network with PNIPAAm included: hydrophilic-hydrophobic transition measured by the partition of Organe II and Methylene Blue in Water." Polymer 44, 2003, pp. 4213-4219.

Hassan, C.M. et al. "Modeling of Crystal Dissolution of Poly(vinyl alcohol) gels produced by freezing/thawing processes." Polymer 41, 2000, pp. 6729-6739.

Hassan, C.M. et al. "Structure and Morphology of Freeze/Thawed PVA Hydrogels," Macromolecules, 2000, pp. 2472-2479, vol. 33, No. 7.

Hickey, A.S. et al. "Solute Diffusion in Poly(vinyl) alcohol/poly(acrylic) acid composite membranes prepared by freezing/thawing techniques." J. Memb. Sci. 107, 1995, pp. 229-237.

Kobayashi, M. et al. "Development of An Artificial Meniscus Using Polyvinyl alcohol-hydrogel for early return to, and continuance of, athletic life in sportspersons with severe meniscus injury." Abstract only, The Knee 10, 2003, p. 53.

Kobayashi, M. et al. "Preliminary Study of Polyvinylalcohol-hydrogel (PVA-H) artificial meniscus." Biomaterials 24, 2003, pp. 639-647.

Lester, C.L. et al. "Physical Properties of Hydrogels Synthesized from Lyotropic Liquid Crystalline Templates" Chem. Mater. 15, 2003, pp. 3376-3384.

Mano, V. et al. "Blends Composed of Poly(N-Isopropylacrylamide) and an Ethylene/Vinyl Alcohol Copolymer: Thermal and Morphological Studies" J. App. Polymer Sci., 2004, pp. 501-505.

Park, J.H. et al. "Hydrogels based on Poly(ethylene oxide) and poly (tetramethylene oxide) or poly)dimethyl siloxane). III. In vivo Biocompatability and Biostability." J. Biomed. Mater. Res. 64A, 2003, pp. 309-319.

Schmedlen, R.H. et al. "Photocrosslinkable polyvinyl alcohol hydrogels that can be modified with cell adhesion peptides for use in tissue engineering." Biomaterials, 23, 2002, pp. 4325-4332.

Suggs, L.J. et al. "In vitro Cytotoxicity and in Vivo Biocompatability of Poly(propylene fumurate-co-ethylene glycol) hydrogels." J. Biomed. Mater. Res., 1999, pp. 22-32, vol. 46.

Thomas, J.D. "Novel Associated PVA/PVDP Hydrogels for Nucleuc Pulposus Replacement." Thesis, Master of Science in Material Engineering Degree, Drexel University, Sep. 2001.

Ushio, K. et al. "Attachment of Artificial Cartilage to Underlying Bone." J. Biomed. Mater. Res. Part B: Appl. Biomater. 68B, 2004, pp. 59-68.

Ushio, K. et al. "Partial Hemiarthroplasty for the treatment of Osteonecrosis of the Femoral Head: An Experimental Study in the Dog." J. Bone Joint Surg., 2003, pp. 922-930, vol. 85B.

Zhang, X. et al. "Synthesis and Characterization of Partially Biodegradable, Temperature and pH Sensitive Dex-MA/PNIPAAm Hydrogels." Biomat., 25, 2004, pp. 4719-4730.

"Lecture 7: Hydrogel Biomaterials: Structure and Physical Chemistry," Spring 2003, 8 pages.

ISR/WO for PCT/US2006/006356 dated Jun. 22, 2006, 9 pages.

EP Search Report for EP06255568.5, Jun. 15, 2007.

Li et al. Anal. Biochem., 256, 130-132 (1998).

Hassan et al. "Structure and Applications of Poly(vinyl Alcohol) Hydrogels Produced by Conventional Crosslinking or by Freezing/Thawing Methods." Advances in Polymer Science, vol. 153, 2000.

Anseth et al. "In situ forming degradable networks and their application in tissue engineering and drug delivery." J. Controlled Release 78 (2002), 199-209, 2002.

Lin-Gibson et al. "Synthesis and Characterization of PEG Dimethacrylates and Their Hydrogels." Biomacromolecules 2004, 5, 1280-1287, 2004.

Rao et al. J. Chem. Soc. Dalton Trans., 2001, 1939-1944.

LeGeros R. Z., "Calcium phosphates in oral biology and medicine," Monograph in Oral Science, vol. 15, pp. 1-201, (1991).

Chow et al.,"Octacalcium Phosphate," Monograph in Oral Science, vol. 18, pp. 94-112 and 130-148, (2001).

Peppas et al. "Physicochemical Foundations and Structural Design of Hydrogels in Medicine and Biology." Ann. Rev. Biomed. Eng. 2, 9-29 (2000).

Hassan et al. "Cellular PVA Hydrogels Produced by Freeze/Thawing." J. Appl. Poly. Sci. 76, 2075 (2000).

Moro et. al. "Surface Grafting of Artificial Joints with Biocompatible Polymer for Preventing Periprosthetic Osteolysis." Nature Materials, 3, 829 (2004).

Hickey et al. :Solute Diffusion in Poly(vinyl)alchohol/poly(acrylic acid) composite membranes prepared by freezing/thawing techniques. Polymer 38, pp. 5931-5936 (1997).

Wang B., et al. The Influence of Polymer concentration on the Radiation-chemical Yield of Intermolecular Crosslinking of Poly(Vinyl Alcohol) by gamma-rays in Deoxygenated Aqueous Solution. Radiation Physics and Chemistry, 2000. 59: p. 91-95.

Rosiak, J. M. & Ulanski, P. Synthesis of hydrogels by irradiation of polymers in aqueous solution, Radiation Physics and Chemistry 1999 55: 139-151.

Stammen, J. A., et al. Mechanical properties of a novel PVA hydrogel in shear and unconfined compression Biomaterials, 2001 22: p. 799-806.

Yamaura, K., et al. Properties of gels obtained by freezing/thawing of poly(vinyl alcohol)/water/dimethyl sulfoxide solutions. Journal of Applied Polymer Science 1989 37:2709-2718.

Lozinsky, V. I. And Damshkaln, L. G. Study of cryostructuration of polymer systems. XVII. Poly(vinyl alcohol) cryogels: Dynamics of cryotropic gel formation. Journal of Applied Polymer Science 2000 77:2017-2023.

Oka M et al. "Development of artificial articular cartilage," Pro. Inst. Mech. Eng. 2000 214:59-68.

EP Search Report for EP 06256525.4 dated May 20, 2007.

Babb et al. "Perfluorcyclobutane Aromatic Ether Polymers. III. Synthesis and . . . " J. Applied. Polymer Sci., vol. 69, (1998), pp. 2005-2012.

Carey et al., Adv. Org. Chem., Part B., p. 892, 2001.

EP Search Report for EP06256452.1 dated May 23, 2007.

ISR/WO for PCT/US2006/046725 dated Jul. 28, 2008.

Park K.R. et al. "Synthesis of PVA/PVP Hydrogels having Two-Layer by Radiation and their Physical Properties." Rad. Phys. and Chem., Jun. 2003, pp. 361-365. vol. 67, No. 3-4.

Hassan C.M. "Diffusional Characteristics of Freeze/Thawed Poly-(vinyl alcohol) hydrogels: Applications to protein controlled release from multilaminate devices." Eur. J. Pharm. and Biopharm., 2000, pp. 161-165, vol. 49.

Bass L.S. "Laser Tissue Welding: A Comprehensive Review of Current and Future Clinical Applications," Lasers in Surgery and Medicine, 1995, pp. 315-349. vol. 17.

ISR/WO for PCT/EP2005/010931 dated February 16, 2006.

ISR/WO for PCT/US2007/064782 dated May 3, 2008.

Bray, J.C. et al. "Poly(vinyl Alchoool) Hydrogels: Formation by Eelctron Beam Irradiation of Aqueous Solutions and Subsequent Crystallization." J. Applied Polymer Sci., vol. 17, pp. 3779-3794, 1973.

Bray, J.C. et al. "Poly(vinyl Alcohol) Hydrogels for Synthetic Articular Cartilage Material, " Biomed. Mater. Res., vol. 7, pp. 431-443, 1973.

Kawanishi, K. Thermodynamic Consideration of the Sol-Gel Transition in Polymer Solutions. 35th Annual Meeting of the Society of Polymer Science, Japan 1986.

Lozinsky, V.I. et al. "Study of Cryostructures of Polymer Systems, XIV. Poly(vinyl alchohol) Cryogels: Apparent Yield of Freeze-Thaw Induced Gelation of Concentrated Aqueous Solutions of the Polymer." J. Applied Polymer Sci., vol. 77, 1822, 1831 (2000).

Lozinsky, V.I. et al. "Study of Cryostructuration of Polymer Systems, XVII. Poly(vinyl alcohol) Cryogels: Dynamics of the Cryotropic Gel Formation." J. Appl. Polymer Sci., vol. 77, 2017-2023 (2000).

Lozinsky, V.I. et al. "Swelling Behavior of poly,(vinyl alcohol) cryogels employed as matrices for cell immobilization." Enzyme Microb. Technol., vol. 18, Issue 8, Jun. 1996. pp. 561-569.

Peppas et al. "Reinforced Uncrosslinkable Poly (vinyl alcohol) gels produced by cyclic freezing-thawing processes: A Short Review." J. Controlled Release, 16 (1991), 305-310.

Mondino, A.V. et al. "Physical properties of gamma irradiated poly (vinyl alcohol) hydrogel preparations" Radiation Physics and chemistry, 55, p. 723,726 (1999).

Urushizaki, F. Swellingand Mechanical Properties of Poly (vinyl alcohol) Hydrogels. Intl. J. Pharma., 58, 135-142, 1990.

Lozinsky, V.I. "On the Possibility of Mechanodestruction of Poly (vinyl Alcohol) Molecules under Moderate Freezing of its Concentrated Water Solutions." Polymer Bulletin, 15, p. 333-340 (1986).

Yokoyama, F. "Morphology and Structure of Highly Elastic Poly (vinyl alcohol) Hydrogel Prepared by Repeated Freezing-and-Melting" Colloid & Polymer Sci. 264, 595-601 (1986).

Covert, R.J. et al. "Friction and Wear Testing of a New Biomaterial for Use as an Articular Cartilage Substitute," BED 50 (2001), 355-356, Bioengineering Conference, ASME 2001.

Ding, Mei Yee. Characterisation of Polyvinyl Alcohol Hydrogels, 2003. Undergraduate Chemical Engineering Thesis, University of Queensland, Brisbane QLD 4072, Australia http://www.cheque.uq.edu.au/ugrad/theses/2003/pdf/CHEE4006/40054522/40054522.pdf (working link on 04/20/1009).

Jaguar-Grodzinski, J. "Biomedical Application of Functional Polymers." Reactive and Functional Polymers 39 (1999) 99-138.

Ulanski, P. et al. "OH-Radical induced crosslinking and strand breakage of poly (vinyl alcohol) in aqueous solution in the absence and presence of oxygen. A pulse radiolysis and product study" Macromol. Chem. Phys. 195, p. 1443-14461 (1994).

International Search Report dated Feb. 2, 2009 for International Patent Application No. PCT/US2008/071435.

MULTI-POLYMER HYDROGELS

TECHNICAL FIELD

The present invention relates generally to a composition comprising multi-polymer hydrogel materials and methods of making the composition, and specifically to an implantable article formed from multi-polymer hydrogel materials.

BACKGROUND

Hydrogels are water-swellable or water-swollen materials having a structure defined by a crosslinked network of hydrophilic homopolymers or copolymers. The hydrophilic homopolymers or copolymers may or may not be water-soluble in free form, but in a hydrogel are rendered insoluble (but swellable) in water due to covalent, ionic, or physical crosslinking. In the case of physical crosslinking, the linking may take the form of entanglements, crystallites, or hydrogen-bonded structures. The crosslinks in a hydrogel provide structure and physical integrity to the network.

Hydrogels have been made from a variety of hydrophilic polymers and copolymers. Poly(ethylene glycol), poly(vinyl pyrrolidone), polyacrylamide, poly(hydroxyethyl methacrylate), and copolymers of the foregoing, are examples of polymers that may be used to make hydrogels. Hydrogels have also been made from biopolymers such as chitosan, agarose, hyaluronic acid and gelatin, in addition from semi-interpenetrating network ("IPN") hydrogels and gelatin crosslinked with poly(ethylene glycol) diacrylate.

Poly(vinyl alcohol) ("PVA") has been studied extensively for potential biomedical applications. PVA hydrogels can be produced, for example, from an aqueous solution via repeated freezing and thawing cycles that increase the order of the crystals, changing the dissolution properties, mesh size, and diffusion properties of the polymer.

Hydrogels have shown promise in biomedical and pharmaceutical applications, due, in part, to their high water content and rubbery or pliable nature, which may mimic natural tissue and may facilitate the release of bioactive substances at a desired physiological site. For example, hydrogels have been used or proposed for use in a variety of tissue treatment applications, including implants, tissue adhesives, bone grafts as well as in meniscus and articular cartilage replacement. Hydrogels may also act as a carrier for delivering bioactive substances including drugs, peptides, and proteins to a physiological site.

However, many biomedical applications require that the implanted article possess different characteristics, such as mechanical and chemical properties, at different locations or surfaces of the article. Thus, there is a need to provide hydrogel materials and articles that present different characteristics at different locations of the implanted article.

SUMMARY OF THE INVENTION

The present invention provides a multi-polymer hydrogel article comprising a first polymeric, water-swellable material and a second polymeric material. The multi-polymer hydrogel article has a first region that substantially comprises the first polymeric, water-swellable material, a second region adjacent the first region that comprises a mixture of the first polymeric, water-swellable material and the second polymeric material, and a third region adjacent the second region that substantially comprises the second polymeric material. The multi-polymer hydrogel article exhibits an increasing concentration gradient in the second polymeric material moving from the first region, through the second region, to the third region.

The present invention also provides a method of forming a multi-polymer hydrogel article. The inventive method comprises forming a hydrogel structure comprising a first polymeric, water-swellable material. An aerogel structure comprising a plurality of open pores is formed by dehydrating the hydrogel structure. The aerogel structure is then contacted with a second polymeric material. The second polymeric material incorporates into at least a portion of the plurality of open pores in the aerogel structure to form a multi-polymer hydrogel article. The resulting multi-polymer hydrogel article is then rehydrated.

DETAILED DESCRIPTION

The present invention provides for a multi-polymer hydrogel article comprising a first polymeric, water-swellable material and a second polymeric material. The multi-polymer hydrogel article is organized into a first, second, and third region, wherein the first region substantially comprises the first polymeric, water-swellable material, the second region adjacent the first region comprises a mixture of the first polymeric, water-swellable material and the second polymeric material, and the third region adjacent the second region substantially comprises the second polymeric material. Further, the second polymeric material exhibits an increasing concentration gradient moving from the first region, through the second region, to the third region. In one embodiment, the second polymeric material is a water-swellable material.

As used in this specification, the terms "water-swellable" or "hydrogel" indicate that the article is able to take on and retain water within a network of polymers.

Suitable water-swellable materials include at least one of a hydrophilic polymer, a homopolymer, a combination of a hydrophilic polymer and a hydrophobic polymer, a blend of polymers, a copolymer, or a thermoplastic material, or combinations thereof. In one embodiment, the water-swellable material is selected from the group consisting of polymers and copolymers of polyvinyl alcohol, polyglycols, polyethylene glycol dimethacrylate, polyethylene glycol diacrylate, polyhydroxyethyl methacrylate, polyvinyl pyrrolidone, polyacrylamide, polyacrylic acid, hydrolyzed polyacrylonitrile, polyethyleneimine, ethoxylated polyethyleneimine, polyallyl alcohol, and polyallylamine, and combinations thereof.

In some embodiments, the second polymeric material is a polyurethane elastomer, silicone elastomer, hydrogel, or lyogel, or combinations thereof. In one embodiment, the first polymeric, water-swellable material and the second polymeric material comprise a common monomer. The second polymeric material may also be water-swellable, with the first and second water-swellable materials being different, with a common monomer or without a common monomer. For example, in one embodiment, the first polymeric, water-swellable material is a polyvinyl alcohol (PVA)/polyethylene-co-vinyl alcohol (EVAL) copolymer and the second polymeric material is polyvinyl alcohol (PVA). In some embodiments, the first polymeric, water-swellable material, the second polymeric material, the aerogel structure, and/or the multi-polymer hydrogel article is thermoplastic. Further examples of suitable materials to be used as the first polymeric, water-swellable material and/or the second polymeric material can be found in U.S. patent application Ser. No. 11/614,389, incorporated by reference herein in its entirety.

The organization of the multi-polymer hydrogel article is such that the first region extends from a first point to a first interface with the second region, the second region extends from the first interface to a second interface with the third region, and the third region extends from the second interface to a second point. Further, the percent volume ratio of the first polymeric, water-swellable material to the second polymeric material is about 100:0 at the first point and about 0:100 at the second point and continuously changes from 100:0 at the first point to 0:100 at the second point. Each of the first and second points may reside at exterior surfaces of the article, or may reside interiorly within the respective first and third regions.

The present invention also provides a method of forming a multi-polymer hydrogel article. The method comprises (a) forming a hydrogel structure comprising a first polymeric, water-swellable material, (b) creating an aerogel structure comprising a plurality of open pores by dehydrating the hydrogel structure, (c) contacting the aerogel structure with a second polymeric material to incorporate the second polymeric material into at least a portion of the plurality of open pores to form a multi-polymer hydrogel article, and (d) rehydrating the multi-polymer hydrogel article.

The method of the present invention may be used to impart desirable characteristics in a hydrogel material or device, such as reinforcing particular areas, providing hoop stress support, creating transition zones between different materials, and/or changing mechanical properties, e.g., compressive modulus, tensile strength, etc.

In one embodiment, forming the hydrogel structure comprises casting, injection molding, or compression molding the first polymeric, water-swellable material into a shape. In another embodiment, forming the hydrogel structure further comprises dip coating, casting or molding the first polymeric, water-swellable material at least partially encompassing a third sacrificial material. In some embodiments, the third sacrificial material is soluble in an aqueous solution. The third sacrificial material may comprise a variety of materials including sugars, waxes, gelatins, salts, low molecular weight water-soluble polymers, ice, and biodegradable polymers, and combinations thereof.

In one embodiment of the present method, the third sacrificial material is dissolved to form a void at least partially encompassed by the first polymeric, water-swellable material. In various embodiments, the third sacrificial material is dissolved in vivo. In one embodiment, the void is limited at its periphery by the first polymeric, water-swellable material such that the first polymeric, water-swellable material substantially surrounds the void. In some embodiments, the first polymeric, water-swellable material forms a balloon or a bubble. The void and/or the hydrogel structure may be tailored to any desired shape and size. In some embodiments, the void created by the third sacrificial material may be at least partially filled with a second polymeric material that is in liquid form. The liquid polymer may be injected by a needle or cannula into the void formed by the third sacrificial material.

In another embodiment, the third sacrificial material is included in the first polymeric, water-swellable material such that when the third sacrificial material is dissolved, open pores are formed in addition to those formed when creating the aerogel structure. In some embodiments, the third sacrificial material is soluble in an aqueous solution. The third sacrificial material may comprise a variety of materials including sugars, waxes, gelatins, salts, low molecular weight water-soluble polymers, ice, and biodegradable polymers, and combinations thereof.

In one embodiment, the formation of the hydrogel structure includes using a surfactant or rapid agitation to create spheres, rods, globules, ellipsoidal shapes, cylindrical shapes, and/or disc-like shapes. In one embodiment, a surfactant is used in the polymerization process to create hydrogel beads, for example, polymerization of hydroxymethylmethacrylate in a surfactant. In another embodiment, the surfactant may be polymerized in a self-emulsifying polymerization to create the hydrogel beads, for example, the polymerization of sodium methacrylate in water. Monomers that may be polymerized in the prescense of surfactants to create hydrogel beads may include glycidyl methacrylate modified hyaluronate, acrylate modified polyethylene glycol, or the polymerization of vinyl acetate followed by post hydrolysis to create polyvinyl alcohol. Suitable surfactants for these polymerizations may include perfluorocarboxlyic acid salts, tetraethylene glycol dodecyl ether, decaethylene glycol hexadecyl ether, carboxylic acid salts, Alkanol®, Merpol®, Brij®, Adogen®, Igepal®, Tergitol®, or Triton®.

The aerogel structure is created by dehydrating, e.g. removing water and/or plasticizers, from the hydrogel structure. It may be understood that dehydration includes partial to complete removal of water and/or plasticizers from the hydrogel structure. In various embodiments, the water and/or plasticizer is removed from the hydrogel structure by, for example, heating, evaporating, subjecting to a vacuum, freeze-drying, or solvent exchange, or combinations thereof. In embodiments where the water and/or plasticizer is partially removed from the hydrogel structure, a semiporous material is created. In some embodiments, after dehydrating the hydrogel structure to create the aerogel structure, the aerogel structure is formed into a desired shape. Forming the aerogel structure includes cutting, molding, and/or shaping the aerogel structure. In some embodiments, water-swellable sheets may be dehydrated before creating a desired shape.

After formation of the aerogel structure, the aerogel structure is contacted with a second polymeric material. As used herein "contacted" includes filling, pressing, interlocking, impregnating, penetrating or intercalating. Furthermore, the aerogel structure may be contacted by the second polymeric material in a variety of ways including immersing at least a portion of the aerogel structure in the second polymeric material, injecting the second polymeric material into at least a portion of the aerogel structure, compressing the second polymeric material into at least a portion of the aerogel structure, and contacting less than the entire surface area of the aerogel structure with the second polymeric material.

In an alternative embodiment, the first polymeric, water-swellable material, absent formation of the aerogel structure, may be contacted with the second polymeric material and introduced into the first polymeric, water-swellable material by solvent bonding techniques. Solvent bonding requires compatible solvents for the first polymeric, water-swellable material and the second polymeric material. The solvent bonding creates an interlocking of the two polymer layers. Compatible solvents may include tetrahydrofuran, toluene, dimethylformamide, dimethylacetamide, acetone, acetonitrile, cyclohexane, cyclopentane, 1,4-dioxane, ethyl acetate, glyme, methyl tert-butyl ether, methyl ethyl ketone, pyridine, water, dimethylsulfoxide, or chlorobenzene, or combination thereof. The subsequent solvent bonded structure formed following contact between the first polymeric, water-swellable material and the second polymeric material is amenable to all the embodiments described herein.

The method of the present invention results in the formation of a multi-polymer hydrogel article comprising the first polymeric, water-swellable material and the second polymeric material. The multi-polymer hydrogel article is organized into a first region substantially comprising the first polymeric, water-swellable material, a second region adjacent the first region comprising a mixture of the first polymeric, water-swellable material and the second polymeric material, and a third region adjacent the second region substantially comprising the second polymeric material. Further, the second polymeric material exhibits an increasing concentration gradient moving from the first region, through the second region, to the third region.

Additionally, the first region extends from a first point to a first interface with the second region, the second region extends from the first interface to a second interface with the third region and includes therein a second point, and the third region extends from the second interface to a third point. In one embodiment, the multi-polymer hydrogel article formed by the present method has a percent volume ratio of the first polymeric, water-swellable material to the second polymeric material that continuously changes from about 100:0 at the first point, to about 50:50 at the second point, to about 0:100 at the third point. In one embodiment, pore blockers are present during the present method such that some portion of the pores in the aerogel structure are resistant to penetration by the second polymeric material. In embodiments where a pore blocker is present, the second point is moved towards the third point in the multi-polymer hydrogel article. Pore blockers that may be used in the present method include sugars, salts, low molecular weight water-soluble polymers, waxes, liquids, and biodegradable polymers, and combinations thereof.

In addition to the incorporation of the second polymeric material into at least a portion of the plurality of open pores in the aerogel structure to form a multi-polymer hydrogel article, in some embodiments, the second polymeric material is also introduced into the void created by dissolving the third sacrificial material such as sugars, salts, or waxes. In another embodiment, a material is introduced into the void created by dissolving the third sacrificial material and may include materials such as lyogels, hydrogels, monomers, beads, urethanes, acrylates, methacrylates, or other injectable polymeric materials or precursors. In various embodiments, the second polymeric material may contact the first polymeric, water-swellable material in situ and/or be cured in situ as part of an implantation procedure or cured ex-vivo before implantation.

In one embodiment, the aerogel structure is contacted with the second polymeric material under pressure. Using the previously described organization of the resultant multi-polymer hydrogel article where the first region extends from a first point to a first interface with the second region, the second region extends from the first interface to a second interface with the third region and includes therein a second point, and the third region extends from the second interface to a third point and where a percent volume ratio of the first polymeric, water-swellable material to the second polymeric material continuously changes from about 100:0 at the first point, to about 50:50 at the second point, to about 0:100 at the third point, the affect of contacting the aerogel structure with the second polymeric material under pressure is to move the second point towards the first point. The extent of the movement of the second point towards the first point is affected by many factors including the amount of pressure exerted on the second polymeric material.

In yet another embodiment of the present method, a multilayered, multi-polymer hydrogel article is produced. In one embodiment, at least one of the method steps (a-d) described above is repeated. For instance, following contacting of the aerogel with the second polymeric material, the resulting aerogel structure incorporating the second polymeric material is dehydrated to form a second aerogel structure. This second aerogel structure can be contacted with a third polymeric material such that the third polymeric material incorporates into at least a portion of the second aerogel structure. The process can be repeated such that n aerogel structures are contacted with n+1 polymeric materials and with each cycle of dehydration and incorporation, another layer is added to the resultant multi-polymer hydrogel article. The n+1 polymeric material can be any of the potential materials described for either the first polymeric, water-swellable material or the second polymeric material. Also, any of the n aerogel structures are subject to the embodiments described above for the aerogel structure. In various embodiments, the multilayers are comprised of different polymeric materials or the same polymeric material. In one embodiment, the multilayered, multi-polymer hydrogel article is composed of variations of the same polymer. For instance, the polymer may vary by concentration, molecular weight, degree of branching, tacticity, extent of crosslinking, etc.

In still another embodiment, the multilayered, multi-polymer hydrogel article can be accomplished utilizing insert-molding techniques known to one skilled in the art. Examples of methods to create the layering may include liquid injection molding. Compression molding may also be used and insures good interlocking of the first polymeric, water-swellable material and the second polymeric material.

In another embodiment, a multilayered, multi-polymer hydrogel article may be formed using solvent bonding by at least partially covering a first polymeric, water-swellable material with a second polymeric material, both containing compatible solvents, to create a multi-polymer hydrogel article. The multi-polymer hydrogel article may then be contacted with a third polymeric material, also containing compatible solvents, resulting in a multilayered, multi-polymer hydrogel article. The process may be repeated such that each cycle of incorporation results in another layer being added to the resultant multi-polymer hydrogel article. In various embodiments, the multilayers are comprised of different polymeric materials or the same polymeric material. In one embodiment, the multilayered, multi-polymer hydrogel article is composed of variations of the same polymer. For instance, the polymer may vary by concentration, molecular weight, extent of crosslinking, etc.

The present method for forming a multi-polymer hydrogel article may also include crosslinking of all or a portion of the multi-polymer hydrogel article. In various embodiments, crosslinking can occur by radiation crosslinking, physical crosslinking, or chemical crosslinking, or combinations thereof. Examples of radiation crosslinking includes exposing the multi-polymer hydrogel article to at least one of visible light radiation, infrared radiation, ultraviolet radiation, electron beam radiation, gamma radiation, or x-ray radiation. An example of physical crosslinking is exposing the multi-polymer hydrogel article to freezing and thawing. Examples of chemical crosslinking includes exposing the multi-polymer hydrogel article to a monoaldehyde or a diisocyanate. Crosslinking may be carried out after forming the hydrogel structure, after forming the multi-polymer hydrogel article, after shaping the multi-polymer hydrogel article into a desired shape, after in situ formation of the article, or at any other suitable point during processing.

The multi-polymer hydrogel article of the present invention may be suitable for use in a wide variety of applications, including tissue replacement or augmentation, biomedical applications, and pharmaceutical applications. Also, the article will have utility for many orthopedic conditions, particularly those that involve repair of a cartilage, repair of soft tissue defects, e.g., treating damaged or diseased hyaline cartilage, replacement of damaged cartilage surface, and use in spinal discs. The article of the present invention can be used as an implant to replace at least a portion of an artificial hip, hip liner, knee, knee liner, disk replacement, shoulder, elbow, foot, ankle, finger, or mandible.

The following examples are provided to illustrate the invention and are not intended to limit the same.

EXAMPLE 1

Synthesis of the First Polymeric, Water-Swellable Material

To a 1000 ml beaker equipped with a mechanical stirrer was added 60 g polyvinyl alcohol, 30 ml deionized water, and 270 ml of dimethylsulfoxide (DMSO). The polyvinyl alcohol was 99+% hydrolyzed with an average molecular weight of 124 kiloDalton (kDa) to 186 kDa and was used as received from Sigma-Aldrich (St. Louis, Mo.). The DMSO was used as received from Sigma-Aldrich and contained ≦0.4% water. The solution was heated to 90° C. for three hours.

After three hours, the solution was poured into one-cm³ aluminum molds. The solution was allowed to cool slowly to room temperature, and the aluminum molds were then placed into a freezer at −30° C. for three hours. The aluminum molds were removed from the freezer.

The resulting material was translucent, flexible, and pliable. The one cm³ polymeric samples were extracted with 700 ml reagent-grade alcohol (ethanol) followed by solvent exchange with deionized water over a three-day period. The resulting material remained translucent, flexible, and pliable.

Dehydration was performed on a vacuum glass Schlenck line by using a freeze-thaw technique in which the sample was frozen followed by evacuation of the liquid vapor phase. The freeze-thaw procedure was performed as follows: the samples were frozen at −196° C. and a dynamic vacuum was placed on the sample as it warmed to room temperature. The freeze-dried samples served as the aerogel structure.

Synthesis of the Second Polymeric Material

To a one-gallon sigma mixer/extruder (Jaygo Incorporated, New Jersey) fitted with a 3 mm fiber die was added 625.89 g polyethylene-co-vinyl alcohol, 100 ml of water, 1350 g DMSO, and 626.79 g polyvinyl alcohol. The materials were mixed at 240° F. (116° C.) for 70 minutes. The polyvinyl alcohol was 99+% hydrolyzed with an average molecular weight of 146,000 to 186,000 and was used as received from Sigma-Aldrich. The polyethylene-co-vinyl alcohol had an ethylene content of 44 mole-percent and was used as received from Sigma-Aldrich. The DMSO was used as received from Sigma-Aldrich and contained ≦0.4% water.

After 70 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Synthesis of the Multi-Polymer Hydrogel Article

The multi-polymer hydrogel article was formed on a Morgan Press ram injection molder G-100T from Morgan Industries Inc. (Long Beach, Calif.). The aerogel structure was placed in an aluminum mold. The second polymeric material pellets were placed into the barrel of the injection molder. The material was injection molded at 270° C. barrel and 280° C. nozzle temperature. Injection pressure was 7000 psi with 18 tons clamping pressure. After injection, the mold was cooled with circulating water at 10° C. for five minutes prior to removing the sample. The multi-polymer hydrogel article was extracted with 700 ml reagent-grade alcohol (ethanol) followed by solvent exchange with deionized water over a three-day period. The resulting multi-polymer hydrogel article showed a transparent material in the middle of the sample (substantially comprising the first polymeric material) transitioning to an opaque material in the periphery (substantially comprising the second polymeric material). The material in the article remained flexible and pliable.

EXAMPLE 2

Synthesis of the First Polymeric, Water-Swellable Material

To a 1000 ml beaker equipped with a mechanical stirrer was added 60 g polyvinyl alcohol, 30 ml deionized water, and 270 ml of DMSO. The polyvinyl alcohol was 99+% hydrolyzed with an average molecular weight of 124 kDa to 186 kDa and was used as received from Sigma-Aldrich. The DMSO was used as received from Sigma-Aldrich and contained ≦0.4% water. The solution was heated to 90° C. for three hours.

After three hours, the solution was cast between two glass plates to create a hydrogel structure as a sheet. The solution was allowed to cool slowly to room temperature, and the plates were then placed into a freezer at −30° C. for three hours. The plates were removed from the freezer.

The resulting material was translucent, flexible, and pliable. The polymeric sample was extracted with 700 ml reagent-grade alcohol (ethanol) followed by solvent exchange with deionized water over a three-day period. The resulting material remained translucent, flexible, and pliable.

Dehydration was performed on a vacuum glass Schlenck line by using a freeze-thaw technique. The samples were frozen at −196° C. and a dynamic vacuum was placed on the sample as it warmed to room temperature. The freeze-dried samples served as the aerogel structure.

Synthesis of the Second Polymeric Material

To a Jaygo one-gallon sigma mixer/extruder fitted with a 3 mm fiber die was added 625.89 g polyethylene-co-vinyl alcohol, 100 ml of water, 1350 g DMSO, and 626.79 g polyvinyl alcohol. The materials were mixed at 240° F. (116° C.) for 70 minutes. The polyvinyl alcohol was 99+% hydrolyzed with an average molecular weight of 146,000 to 186,000 and was used as received from Sigma-Aldrich. The polyethylene-co-vinyl alcohol had an ethylene content of 44 mole-percent and was used as received from Sigma-Aldrich. The DMSO was used as received from Sigma-Aldrich and contained ≦0.4% water.

After 70 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Synthesis of the Multi-Polymer Hydrogel Article

The multi-polymer hydrogel article was formed on a Morgan-Press G-100T ram injection molder. The aerogel structure was placed in an aluminum mold. The second polymeric material pellets were placed into the barrel of the injection molder. The material was injection molded at 270° C. barrel and 280° C. nozzle temperature. Injection pressure was 7000 psi with 18 tons clamping pressure. After injection, the mold was cooled with circulating water at 10° C. for five minutes prior to removing the sample. The multi-polymer hydrogel article was extracted with 700 ml reagent-grade alcohol (ethanol) followed by solvent exchange with deionized water over a three-day period. The resulting multi-polymer hydrogel article showed a transparent material in the middle of the sample (substantially comprising the first polymeric material) transitioning to an opaque material in the periphery (substantially comprising the second polymeric material). The multi-polymer hydrogel article remained flexible and pliable.

EXAMPLE 3

Synthesis of the First Polymeric, Water-Swellable Material

To a 1000 ml beaker equipped with a mechanical stirrer was added 20 g polyvinyl alcohol, 10 ml deionized water, and 170 ml of DMSO. The polyvinyl alcohol was 99+% hydrolyzed with an average molecular weight of 124 kDa to 186 kDa and was used as received from Sigma-Aldrich. The DMSO was used as received from Sigma-Aldrich and contained ≦0.4% water. The solution was heated to 80° C. for three hours.

After three hours, the solution was poured into a 50 ml flask to form a ¼ inch layer. The layer was allowed to cool to room temperature. A molded piece of sugar was placed on top of the layer and additional polymer solution was poured on top of the layer to form the hydrogel structure. The hydrogel structure was quickly frozen to −30° C. in a methanol/liquid nitrogen slush bath. The hydrogel structure was allowed to warm to room temperature over a two hour period. The hydrogel structure was submersed in methanol for 12 hours followed by solvent exchange in water for three days to dissolve the sugar. The hydrogel structure was then dehydrated and vacuum dried to produce a void.

Synthesis of the Second Polymeric Material

To a 50 ml beaker equipped with a mechanical stirrer was added 15 ml DMSO, 1 ml deionized water, 1.5 g polyvinyl alcohol and 1 g polyethylene-co-vinyl alcohol. The materials were mixed at 80° C. for 3 hours.

Synthesis of the Multi-Polymer Hydrogel Article

The second polymeric material was injected into the void created by the sugar using an 18-gauge needle and syringe. The final article was placed in water for solvent exchange. The subsequent article was cross-sectioned showing that the void was in fact filled with the second polymeric material and the material was attached to the first polymeric material.

Characterization

Mechanical performance properties for selected hydrogels were measured on a Model 3345 from Instron Corporation. The sample from Example 1 showed a push out strength of 1649 psi, which indicates that the first polymeric, water-swellable material and the second polymeric material are interlocked. Push out strength refers to the amount of force required to separate the first polymeric material from the second polymeric material. In this case, the two materials have different mechanical strengths. The high push out strength shows that the two materials were in fact bound together.

What is claimed is:

1. A method of forming a multi-polymer hydrogel article comprising:
   (a) forming a hydrogel structure comprising a first polymeric, water-swellable material,
   (b) creating an aerogel structure comprising a plurality of open pores by dehydrating the hydrogel structure,
   (c) contacting the aerogel structure with a second polymeric material to incorporate the second polymeric material into at least a portion of the plurality of open pores to form the multi-polymer hydrogel article, and
   (d) rehydrating the multi-polymer hydrogel article.

2. The method of claim 1, wherein forming the hydrogel structure comprises dip coating, casting, injection molding, or compression molding the first polymeric, water-swellable material into a shape.

3. The method of claim 2, wherein forming the hydrogel structure further comprises dip coating, casting or molding the first polymeric, water-swellable material at least partially encompassing a third sacrificial material.

4. The method of claim 3, wherein the third sacrificial material is soluble in an aqueous solution.

5. The method of claim 3, wherein the third sacrificial material is selected from the group consisting of sugars, waxes, gelatins, salts, low molecular weight water-soluble polymers, ice, and biodegradable polymers, and combinations thereof.

6. The method of claim 3, further comprising dissolving the third sacrificial material to form a void at least partially encompassed by the first polymeric, water-swellable material.

7. The method of claim 6, wherein the void is limited at its periphery by the first polymeric, water-swellable material such that the first polymeric, water-swellable material substantially surrounds the void.

8. The method of claim 6, wherein dissolving the third sacrificial material occurs in vivo.

9. The method of claim 1, further comprising, prior to forming the hydrogel structure, introducing a third sacrificial material into the first polymeric, water-swellable material, and wherein creating the aerogel structure further includes dissolving the third sacrificial material to thereby form additional open pores.

10. The method of claim 9, wherein the third sacrificial material is soluble in an aqueous solution.

11. The method of claim 9, wherein the third sacrificial material is selected from the group consisting of sugars, waxes, gelatins, salts, low molecular weight water-soluble polymers, ice, and biodegradable polymers, and combinations thereof.

12. The method of claim 1, wherein forming the hydrogel structure further comprises using a surfactant or rapid agitation to create spheres, rods, globules, ellipsoidal shapes, cylindrical shapes, or disc shapes.

13. The method of claim 12, further comprising polymerizing the surfactant in the case of a self emulsifying polymerization to create hydrogel beads.

14. The method of claim 1, wherein dehydrating the hydrogel structure includes removing water and/or plasticizers from the hydrogel structure by heating, subjecting to a vacuum, solvent exchange, or freeze-drying, or combinations thereof.

15. The method of claim 1, wherein creating the aerogel structure further comprises forming the aerogel structure following dehydrating the hydrogel structure, wherein forming comprises cutting, molding, and/or shaping the aerogel structure.

16. The method of claim 1, wherein the contacting results in a first region substantially comprising the first polymeric, water-swellable material, a second region adjacent the first region comprising a mixture of the first polymeric, water-swellable material and the second polymeric material, and a third region adjacent the second region substantially comprising the second polymeric material, wherein the second polymeric material exhibits an increasing concentration gradient moving from the first region, through the second region, to the third region.

17. The method of claim 16 wherein the first region extends from a first point to a first interface with the second region, the second region extends from the first interface to a second interface with the third region and includes therein a second point, and the third region extends from the second interface to a third point; wherein a percent volume ratio of the first polymeric, water-swellable material to the second polymeric material continuously changes from about 100:0 at the first point, to about 50:50 at the second point, to about 0:100 at the third point; and wherein the presence of pore blockers moves the second point towards the third point.

18. The method of claim 17 wherein the pore blockers are selected from the group consisting of sugars, salts, low molecular weight water-soluble polymers, and biodegradable polymers, and combinations thereof.

19. The method of claim 1, wherein contacting the aerogel structure with the second polymeric material further comprises introducing the second polymeric material into a void created by dissolving a third sacrificial material.

20. The method of claim 19, further comprising introducing a material into the void created by dissolving the third sacrificial material.

21. The method of claim 1, wherein contacting the aerogel structure with the second polymeric material occurs under a pressure.

22. The method of claim 21 wherein a first region extends from a first point to a first interface with a second region, the second region extends from the first interface to a second interface with a third region and includes therein a second point, and the third region extends from the second interface to a third point; wherein a percent volume ratio of the first polymeric, water-swellable material to the second polymeric material continuously changes from about 100:0 at the first point, to about 50:50 at the second point, to about 0:100 at the third point; and wherein the extent of the pressure of the second polymeric material moves the second point towards the first point.

23. The method of claim 1 wherein at least two of the steps (a)-(d) are repeated to produce a multilayered, multi-polymer hydrogel article.

24. The method of claim 1 further comprising crosslinking the multi-polymer hydrogel article.

25. The method of claim 24 wherein crosslinking occurs by radiation crosslinking, physical crosslinking, or chemical crosslinking, or combinations thereof.

26. The method of claim 25 wherein radiation crosslinking comprises exposing the multi-polymer hydrogel article to at least one of visible light radiation, ultraviolet radiation, infrared radiation, electron beam radiation, gamma radiation, or x-ray radiation.

27. The method of claim 25 wherein physical crosslinking comprises exposing the multi-polymer hydrogel article to freezing and thawing.

28. The method of claim 25 wherein chemical crosslinking comprises exposing the multi-polymer hydrogel article to a monoaldehyde or a diisocyanate.

* * * * *